US012458787B2

(12) United States Patent
Sathe

(10) Patent No.: US 12,458,787 B2
(45) Date of Patent: Nov. 4, 2025

(54) MEDICAL DEVICE CAP FOR DRUG TRANSFER ASSEMBLY

(71) Applicant: Becton, Dickinson and Company, Franklin Lakes, NJ (US)

(72) Inventor: Tushar R. Sathe, Cedar Knolls, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 209 days.

(21) Appl. No.: 17/885,999

(22) Filed: Aug. 11, 2022

(65) Prior Publication Data

US 2022/0379105 A1 Dec. 1, 2022

Related U.S. Application Data

(63) Continuation of application No. 16/508,874, filed on Jul. 11, 2019, now Pat. No. 11,446,479, which is a (Continued)

(51) Int. Cl.
*A61M 39/20* (2006.01)

(52) U.S. Cl.
CPC ..... *A61M 39/20* (2013.01); *A61M 2205/3561* (2013.01); *A61M 2205/3592* (2013.01); (Continued)

(58) Field of Classification Search
CPC .. A61M 39/20; A61M 39/162; A61M 39/165; A61M 2205/3561;
(Continued)

(56) References Cited

U.S. PATENT DOCUMENTS 4,432,764 A 2/1984 Lopez
5,301,843 A * 4/1994 Groene ............ B05C 17/00516 222/562
(Continued)

FOREIGN PATENT DOCUMENTS

CN 1911739 A 2/2007
JP 2009536562 A 10/2009
(Continued)

*Primary Examiner* — James D Ponton
*Assistant Examiner* — John A Doubrava
(74) *Attorney, Agent, or Firm* — The Webb Law Firm

(57) ABSTRACT

A medical device cap that protectively surrounds a medical device component for disinfection purposes and includes an identification element that can record and transmit pertinent information of the medical device cap and the medical device component is disclosed. The medical device cap enables documentation of instances when the cap is used and promotes stronger compliance with the use of medical device caps for applications involving disinfection of a medical device component such as an IV access port or a luer tip. Use of the medical device cap results in better compliance and monitoring of the use of such caps and leads to reduced incidence of CRBSI infections related to medical device component contamination. In one embodiment, the medical device cap enables automated real-time electronic documentation of when the cap is applied, while also documenting duration of application and tracking of device for inventory management.

15 Claims, 7 Drawing Sheets

Related U.S. Application Data continuation of application No. 14/863,593, filed on Sep. 24, 2015, now Pat. No. 10,413,716.

(60) Provisional application No. 62/057,001, filed on Sep. 29, 2014.

(52) U.S. Cl.
CPC ............... *A61M 2205/6054* (2013.01); *A61M 2205/6063* (2013.01); *A61M 2205/6072* (2013.01)

(58) Field of Classification Search
CPC .. A61M 2205/3592; A61M 2205/6054; A61M 2205/6063; A61M 2205/6072
See application file for complete search history.

(56) References Cited

U.S. PATENT DOCUMENTS

| | | | | |
|---|---|---|---|---|
| 7,780,794 | B2 | 8/2010 | Rogers et al. | |
| 10,413,716 | B2 | 9/2019 | Sathe | |
| 2004/0008123 | A1 | 1/2004 | Carrender et al. | |
| 2004/0073189 | A1 | 4/2004 | Wyatt et al. | |
| 2007/0112333 | A1 | 5/2007 | Hoang et al. | |
| 2007/0287989 | A1 | 12/2007 | Crawford et al. | |
| 2007/0293818 | A1 * | 12/2007 | Stout | G09F 3/0291 604/93.01 |
| 2007/0293822 | A1 * | 12/2007 | Crawford | G09F 3/0291 604/175 |
| 2009/0028750 | A1 * | 1/2009 | Ryan | A61L 2/18 422/292 |
| 2009/0137969 | A1 | 5/2009 | Colantonio et al. | |
| 2009/0257910 | A1 | 10/2009 | Segal | |
| 2011/0044850 | A1 | 2/2011 | Solomon et al. | |
| 2011/0054440 | A1 | 3/2011 | Lewis | |
| 2011/0111794 | A1 | 5/2011 | Bochenko et al. | |
| 2011/0184382 | A1 | 7/2011 | Cady | |
| 2012/0216359 | A1 | 8/2012 | Rogers et al. | |
| 2013/0204227 | A1 | 8/2013 | Bochenko et al. | |
| 2014/0074038 | A1 | 3/2014 | Ivosevic | |
| 2014/0276213 | A1 * | 9/2014 | Bochenko | A61M 39/0208 600/573 |

FOREIGN PATENT DOCUMENTS

| | | | |
|---|---|---|---|
| JP | 2009545399 | A | 12/2009 |
| JP | 2010184087 | A | 8/2010 |
| JP | 2012120852 | A | 6/2012 |
| JP | 2014513569 | A | 6/2014 |
| WO | 2007134066 | A2 | 11/2007 |
| WO | 2011056888 | A2 | 5/2011 |
| WO | 2013130891 | A1 | 9/2013 |
| WO | 2013130891 | A8 | 9/2013 |
| WO | 2014138122 | A2 | 9/2014 |
| WO | 2014145906 | A2 | 9/2014 |

* cited by examiner

MEDICAL DEVICE CAP FOR DRUG TRANSFER ASSEMBLY

CROSS-REFERENCE TO RELATED APPLICATION

The present application is a continuation of U.S. patent application Ser. No. 16/508,874, entitled "Medical Device Cap for Drug Transfer Assembly", filed Jul. 11, 2019, which is a continuation of U.S. patent application Ser. No. 14/863,593, entitled "Medical Device Cap for Drug Transfer Assembly", filed Sep. 24, 2015 (now U.S. Pat. No. 10,413,716), which claims priority to U.S. Provisional Application Ser. No. 62/057,001, entitled "Medical Device Cap for Drug Transfer Assembly", filed Sep. 29, 2014, the entire disclosures of each of which are hereby incorporated by reference.

BACKGROUND OF THE INVENTION

1. Field of the Disclosure

The present disclosure relates generally to components of a drug transfer assembly. More particularly, the present disclosure relates to a medical device cap for protectively surrounding and shielding a medical device component and that includes an identification element that records and transmits information.

2. Description of the Related Art

Disposable antimicrobial sanitizing caps that couple with an IV access port are used for applications involving disinfection of the IV access port. Such devices have been designed to reduce the incidence of Catheter Related Blood Stream Infections (CRBSI) by swabbing and protecting the port to prevent and eliminate microbial migration from the surface of the port to the blood stream. However, not properly cleaning and disinfecting the IV access port may contribute to CRBSI infections.

CRBSI infections have a tremendous cost impact on health care institutions. Furthermore, these institutions are not able to easily track the compliance around disinfection of IV access ports between access of the ports. As medical practitioner shifts change in certain acute care settings, such as the ICU, inaccurate or incomplete records may be handed off from one medical practitioner to another. As such, the health care institution may be unable to track the compliance and utilization of technologies, such as protector caps to reduce CRBSI incidents.

SUMMARY OF THE INVENTION

The present disclosure provides a medical device cap that protectively surrounds a medical device component for disinfection purposes and includes an identification element that can record and transmit pertinent information of the medical device cap and the medical device component. The medical device cap of the present disclosure enables documentation of instances when the cap is used and promotes stronger compliance with the use of medical device caps for applications involving disinfection of a medical device component such as an IV access port or a luer tip. In this manner, use of the medical device cap of the present disclosure results in better compliance and monitoring of the use of such caps and leads to reduced incidence of CRBSI infections related to medical device component contamination. In one embodiment, the medical device cap enables automated real-time electronic documentation of when the cap is applied, while also documenting duration of application and tracking of the device for inventory management.

In accordance with an embodiment of the present invention, an IV access port cap for a drug transfer assembly includes a cap body removably connectable with an IV access port and an identification element disposed on the cap body, wherein with the cap body connected to the IV access port, the identification element records information.

In one configuration, with the cap body connected to the IV access port, the identification element transmits the information to a receiver. In another configuration, with the cap body removed from the IV access port, the identification element records additional information. In yet another configuration, with the cap body removed from the IV access port, the identification element transmits the additional information to a receiver. In one configuration, with the cap body connected to the IV access port, the cap body protectively surrounds at least a portion of the IV access port. In another configuration, the identification element comprises a barcode. In yet another configuration, the identification element comprises an RFID. In one configuration, the information is time duration. In another configuration, the information is frequency information. In yet another configuration, at least a part of the information comprises IV access port cap information. In one configuration, the IV access port cap further includes a disinfecting sponge disposed inside the cap body.

In accordance with another embodiment of the present invention, a medical device cap for a drug transfer assembly includes a cap body removably connectable with a luer tip and an identification element disposed on the cap body, wherein with the cap body connected to the luer tip, the identification element records information.

In one configuration, with the cap body connected to the luer tip, the identification element transmits the information. In another configuration, with the cap body removed from the luer tip, the identification element records additional information. In yet another configuration, with the cap body removed from the luer tip, the identification element transmits the additional information to a receiver. In one configuration, with the cap body connected to the luer tip, the cap body protectively surrounds at least a portion of the luer tip. In another configuration, the identification element comprises a barcode. In yet another configuration, the identification element comprises an RFID. In one configuration, the information is time duration. In another configuration, the information is frequency information. In yet another configuration, at least a part of the information comprises medical device cap information. In one configuration, the medical device cap further includes a disinfecting sponge disposed inside the cap body.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
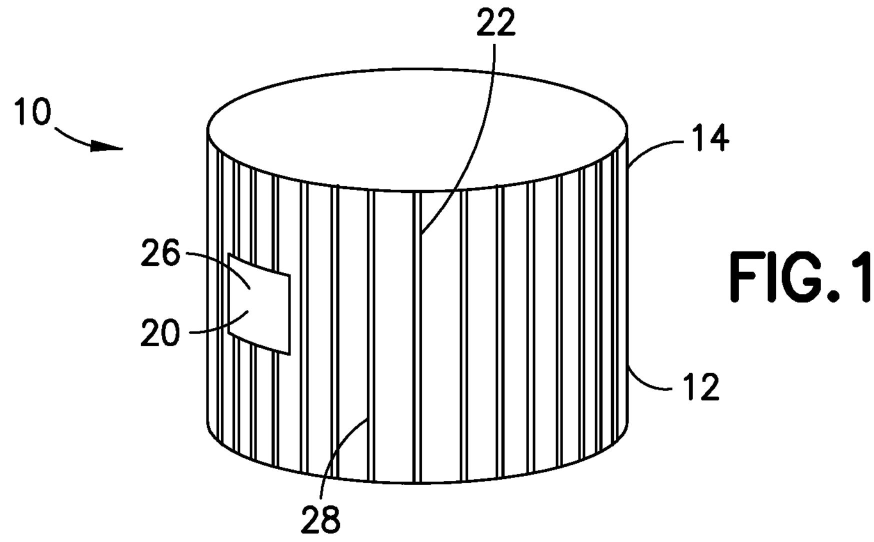
FIG. 1 is a perspective view of a medical device cap of a drug transfer assembly in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms “upper”, “lower”, “right”, “left”, “vertical”, “horizontal”, “top”, “bottom”, “lateral”, “longitudinal”, and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 4:
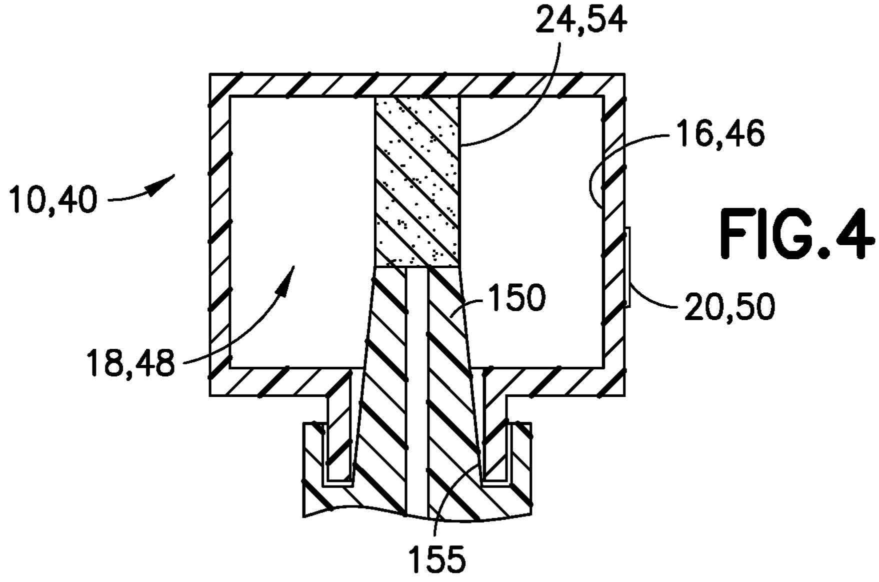
FIG. 4 is a cross-sectional view of a medical device cap connected to a luer tip in accordance with an embodiment of the present invention.
Figure 5:
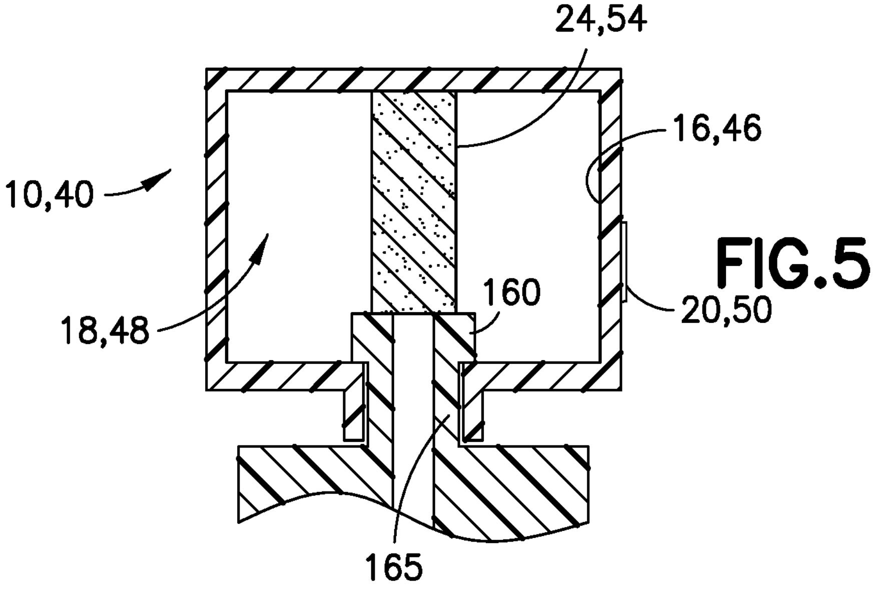
FIG. 5 is a cross-sectional view of a medical device cap connected to an IV access port in accordance with an embodiment of the present invention.

FIG. 1 illustrates a medical device cap 10 according to an exemplary embodiment of the present disclosure. The medical device cap 10 generally includes a cap body 12 defining a cap exterior wall 14 and a cap interior wall 16, respectively corresponding to the exterior profile and the interior profile of medical device cap 10. Referring to FIGS. 4 and 5, the cap interior wall 16 defines a cavity 18 which is sized and shaped to receive a medical device component therein as described in more detail below. The cap body 12 includes an identification element 20 disposed on the cap body 12 for recording and transmitting information as discussed below. In one embodiment, the identification element 20 is disposed on the cap exterior wall 14 of the cap body 12.

The cap exterior wall 14 may include a plurality of grip elements 22 extending around a periphery of the cap body 12 to facilitate the handling of the medical device cap 10 by a medical practitioner. In one embodiment, the plurality of grip elements 22 include ribs 28 which provide a gripping means to allow a medical practitioner to more easily grasp the medical device cap 10 when connecting the medical device cap 10 to a medical device component. The grip elements 22 also provide a gripping means to allow a medical practitioner to more easily grasp the medical device cap 10 when removing the medical device cap 10 from a medical device component. Referring to FIGS. 4 and 5, the medical device cap 10 includes a disinfecting sponge 24 disposed within the cavity 18. The disinfecting sponge 24 includes powerful cleaning and disinfecting agents that are released to contact a medical device component when the medical device cap 10 is connected to a medical device component. For example, referring to FIGS. 4 and 5, with a medical device cap 10 connected to a respective luer tip 150 or IV access port 160, the disinfecting sponge 24 contacts the respective luer tip 150 or IV access port 160 thereby releasing the powerful cleaning and disinfecting agents to the respective luer tip 150 or IV access port 160.

In one embodiment, the identification element 20 is a radio-frequency identification (RFID) element 26 that is disposed on the cap exterior wall 14 of the cap body 12 as shown in FIG. 1. In one embodiment, the RFID element 26 is a passive RFID label on the cap exterior wall 14 that is capable of emitting a signal when in close proximity to an active RFID label on the patient, or on the medical device component such as the IV access port or the luer tip. In this manner, the RFID element 26 is able to record and transmit compliance information related to the medical device cap 10 and/or the medical device component automatically upon connection of the medical device cap 10 with the medical device component. The identification element 20 may be adapted to transmit the information to a receiver, such as a scanner 180. The transmission of information may occur automatically, or may occur upon activation of the identification element 20. Additionally, the RFID element 26 is able to record and transmit compliance information related to the medical device cap 10 and/or the medical device component automatically upon removal of the medical device cap 10 from the medical device component.

The RFID element 26 of the medical device cap 10 is capable of recording and transmitting pertinent information of the medical device cap 10 and the medical device component. The medical device cap 10 that includes the RFID element 26 enables documentation of instances when the medical device cap 10 is used and promotes stronger compliance with the use of the medical device cap 10 for applications involving disinfection of a medical device component such as an IV access port or a luer tip. In this manner, use of the medical device cap 10 that includes the RFID element 26 results in better compliance and monitoring of the use of the medical device cap 10 and leads to reduced incidence of CRBSI infections related to medical device component contamination. In one embodiment, the medical device cap 10 that includes the RFID element 26 enables automated real-time electronic documentation of when the medical device cap 10 is connected to a medical device component, while also documenting duration of application and tracking of device for inventory management.

The medical device cap 10 of the present disclosure also provides a medical device cap that protectively surrounds a medical device component for disinfection purposes. Referring to FIGS. 3-7, the medical device cap 10 protectively surrounds and shields a medical device component to prevent contact between the medical device component and an undesired surface and to prevent contamination of the medical device component of the drug transfer assembly 100. With the medical device cap 10 connected to the medical device component, the medical device component is protectively shielded from exposure to the environment and the medical device cap 10 is prevented from becoming contaminated with undesirables.

The cap body 12 of an exemplary embodiment is preferably made of a pliable material, such as a soft rubber or pliable plastic, for example. In one exemplary embodiment, the cap body 12 is made from thermoplastic elastomers such as styrenic block copolymers, polyolefin blends & alloys, thermoplastic polyurethanes, thermoplastic copolyesters, thermoplastic polyamides, or similar materials. In other embodiments, the cap body 12 is made from thermosetting elastomers (rubbers) such as silicone, polyisoprene, neoprene, or similar materials. The cap body 12 may be injection molded using TPE elastomers or liquid rubber injected or casted using silicones.

In one embodiment, the medical device cap 10 is removably connectable with a medical device component. For example, the medical device cap 10 is removably connectable with a luer tip 150 as shown in FIG. 4. In another embodiment, the medical device cap 10 is removably connectable with an IV access port 160 as shown in FIG. 5. In other embodiments, the medical device cap 10 is removably connectable with other medical device components. For example, the medical device cap 10 is compatible with other components of closed system drug transfer devices.

In one embodiment, the medical device cap 10 could be packaged separately from the other components of a drug transfer assembly 100. In another embodiment, the medical device cap 10 could be "pre-packaged" and come already attached to a medical device component of a drug transfer assembly 100. In one embodiment, the medical device cap 10 could be a disposable cap.

Figure 2B:
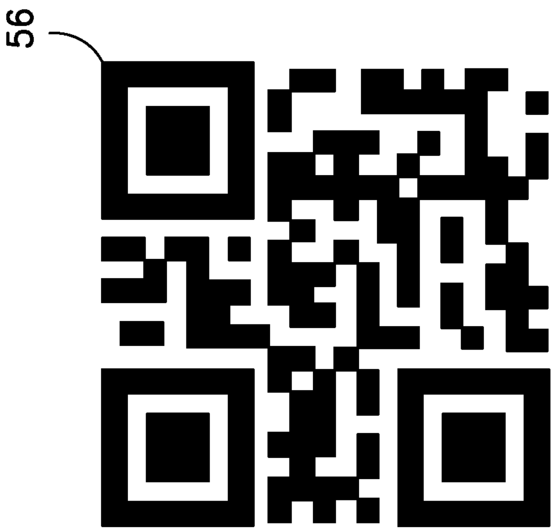
FIG. 2B is an enlarged view of a barcode of the medical device cap of FIG. 2A in accordance with an embodiment of the present invention.
Figure 2A:
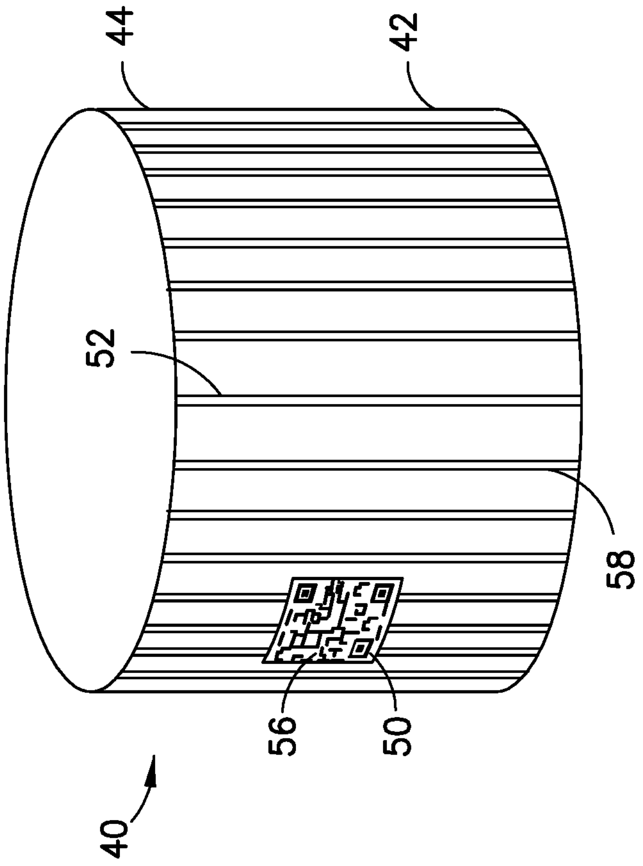
FIG. 2A is a perspective view of a medical device cap of a drug transfer assembly in accordance with another embodiment of the present invention.
Figure 3:
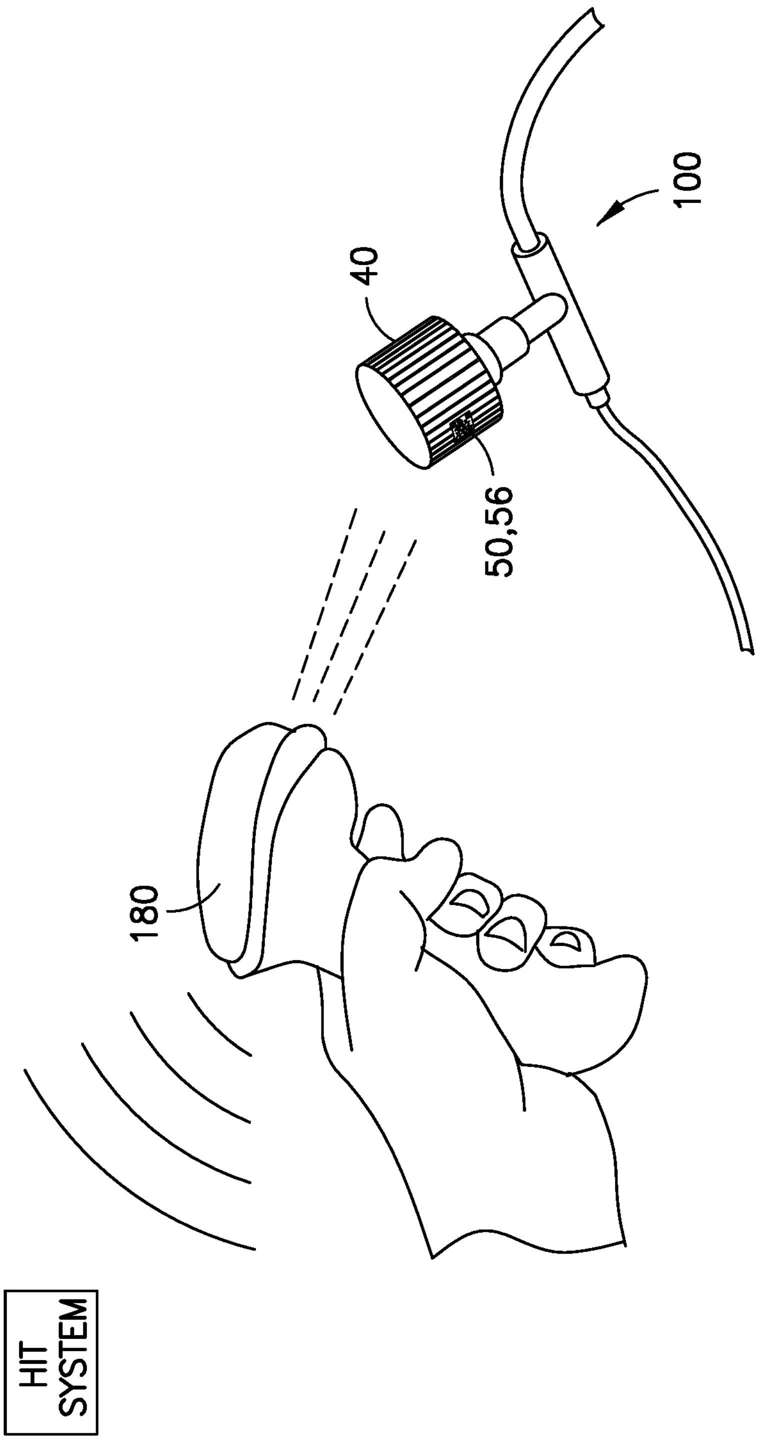
FIG. 3 is a perspective view of the medical device cap of FIG. 2A connected to an IV access port and a scanner reading the barcode of the medical device cap in accordance with an embodiment of the present invention.

FIG. 2A illustrates a medical device cap 40 according to another exemplary embodiment of the present disclosure. The medical device cap 40 generally includes a cap body 42 defining a cap exterior wall 44 and a cap interior wall 46 (FIGS. 4-6), respectively corresponding to the exterior profile and the interior profile of the medical device cap 40. Referring to FIGS. 4 and 5, the cap interior wall 46 defines a cavity 48 which is sized and shaped to receive a medical device component therein as described in more detail below. The cap body 42 includes an identification element 50 disposed on the cap body 42 for recording and transmitting information as discussed below. In one embodiment, the identification element 50 is disposed on the cap exterior wall 44 of the cap body 42.

The cap exterior wall 44 may include a plurality of grip elements 52 extending around a periphery of the cap body 42 to facilitate the handling of the medical device cap 40 by a medical practitioner. In one embodiment, the plurality of grip elements 52 includes ribs 58 which provide a gripping means to allow a medical practitioner to more easily grasp the medical device cap 40 when connecting the medical device cap 40 to a medical device component. The grip elements 52 also provide a gripping means to allow a medical practitioner to more easily grasp the medical device cap 40 when removing the medical device cap 40 from a medical device component. Referring to FIGS. 4 and 5, the medical device cap 40 includes a disinfecting sponge 54 disposed within the cavity 48. The disinfecting sponge 54 includes powerful cleaning and disinfecting agents that are released to contact a medical device component when the medical device cap 40 is connected to a medical device component. For example, referring to FIGS. 4 and 5, with a medical device cap 40 connected to a respective luer tip 150 or IV access port 160, the disinfecting sponge 54 contacts the respective luer tip 150 or IV access port 160 thereby releasing the powerful cleaning and disinfecting agents to the respective luer tip 150 or IV access port 160.

In one embodiment, the identification element 50 is a barcode 56 that is disposed on the cap exterior wall 44 of the cap body 42 as shown in FIGS. 2A and 2B. In one embodiment, the medical device cap 40 includes a unique barcode label 56 and is able to record and transmit compliance information related to the medical device cap 40 and/or the medical device component upon connection of the medical device cap 40 with the medical device component. Additionally, the barcode 56 is able to record and transmit compliance information related to the medical device cap 40 and/or the medical device component upon removal of the medical device cap 40 from the medical device component.

For example, when a medical practitioner connects the medical device cap 40 to a medical device component, such as an IV access port, the medical practitioner can scan the barcode 56 of the medical device cap 40 with a scanner 180 (FIG. 3) to record the unique ID assigned to that particular medical device cap 40 with a time stamp. When it is time to remove the medical device cap 40 to administer medication, or replace with a new medical device cap, the barcode 56 of the medical device cap 40 will be scanned again to record the duration and frequency of medical device caps used throughout a patient's hospital or in-patient stay.

Alternatively, the scanner can reside either separately with the medical practitioner, attached to a BCMA machine, or reside independently on the patient near the medical device component such as an IV access port. Examples of an IV access port include a peripheral IV catheter, a peripherally inserted central catheter, or a central venous catheter.

The barcode 56 of the medical device cap 40 is capable of recording and transmitting pertinent information of the medical device cap 40 and the medical device component. The medical device cap 40 that includes the barcode 56 enables documentation of instances when the medical device cap 40 is used and promotes stronger compliance with the use of the medical device cap 40 for applications involving disinfection of a medical device component such as an IV access port or a luer tip. In this manner, use of the medical device cap 40 that includes the barcode 56 results in better compliance and monitoring of the use of the medical device cap 40 and leads to reduced incidence of CRBSI infections related to medical device component contamination. In one embodiment, the medical device cap 40 that includes the barcode 56 enables automated real-time electronic documentation of when the medical device cap 40 is connected to a medical device component, while also documenting duration of application and tracking of device for inventory management.

The medical device cap 40 of the present disclosure also provides a medical device cap that protectively surrounds a medical device component for disinfection purposes. Referring to FIGS. 3-7, the medical device cap 40 protectively surrounds and shields a medical device component to prevent contact between the medical device component and an undesired surface and to prevent contamination of the medical device component of the drug transfer assembly 100. With the medical device cap 40 connected to the medical device component, the medical device component is protectively shielded from exposure to the environment and the medical device cap 40 is prevented from becoming contaminated with undesirables.

The cap body 42 of an exemplary embodiment is preferably made of a pliable material, such as a soft rubber or pliable plastic, for example. In one exemplary embodiment, the cap body 42 is made from thermoplastic elastomers such as styrenic block copolymers, polyolefin blends and alloys, thermoplastic polyurethanes, thermoplastic copolyesters, thermoplastic polyamides, or similar materials. In other embodiments, the cap body 42 is made from thermosetting elastomers such as silicone, polyisoprene, neoprene, or similar materials. The cap body 42 may be injection molded using TPE elastomers or liquid rubber injected or casted using silicones.

In one embodiment, the medical device cap 40 is removably connectable with a medical device component. For example, the medical device cap 40 is removably connectable with a luer tip 150 as shown in FIG. 4. In another embodiment, the medical device cap 40 is removably connectable with an IV access port 160 as shown in FIG. 5. In other embodiments, the medical device cap 40 is removably connectable with other medical device components. For example, the medical device cap 40 is compatible with other components of closed system drug transfer devices.

In one embodiment, the medical device cap 40 could be packaged separately from the other components of a drug transfer assembly 100. In another embodiment, the medical device cap 40 could be pre-packaged and be provided as already attached to a medical device component of a drug transfer assembly 100. In one embodiment, the medical device cap 40 could be a disposable cap.

As discussed above, a medical device cap 10, 40 of the present disclosure is removably connectable with a medical device component. For example, in one embodiment, the medical device cap 10, 40 is removably connectable with a luer tip 150 as shown in FIG. 4. In another embodiment, the medical device cap 10, 40 is removably connectable with an IV access port 160 as shown in FIG. 5. In other embodiments, the medical device cap 40 is removably connectable with other medical device components. For example, the medical device cap 40 is compatible with other components of closed system drug transfer devices.

Figure 6:
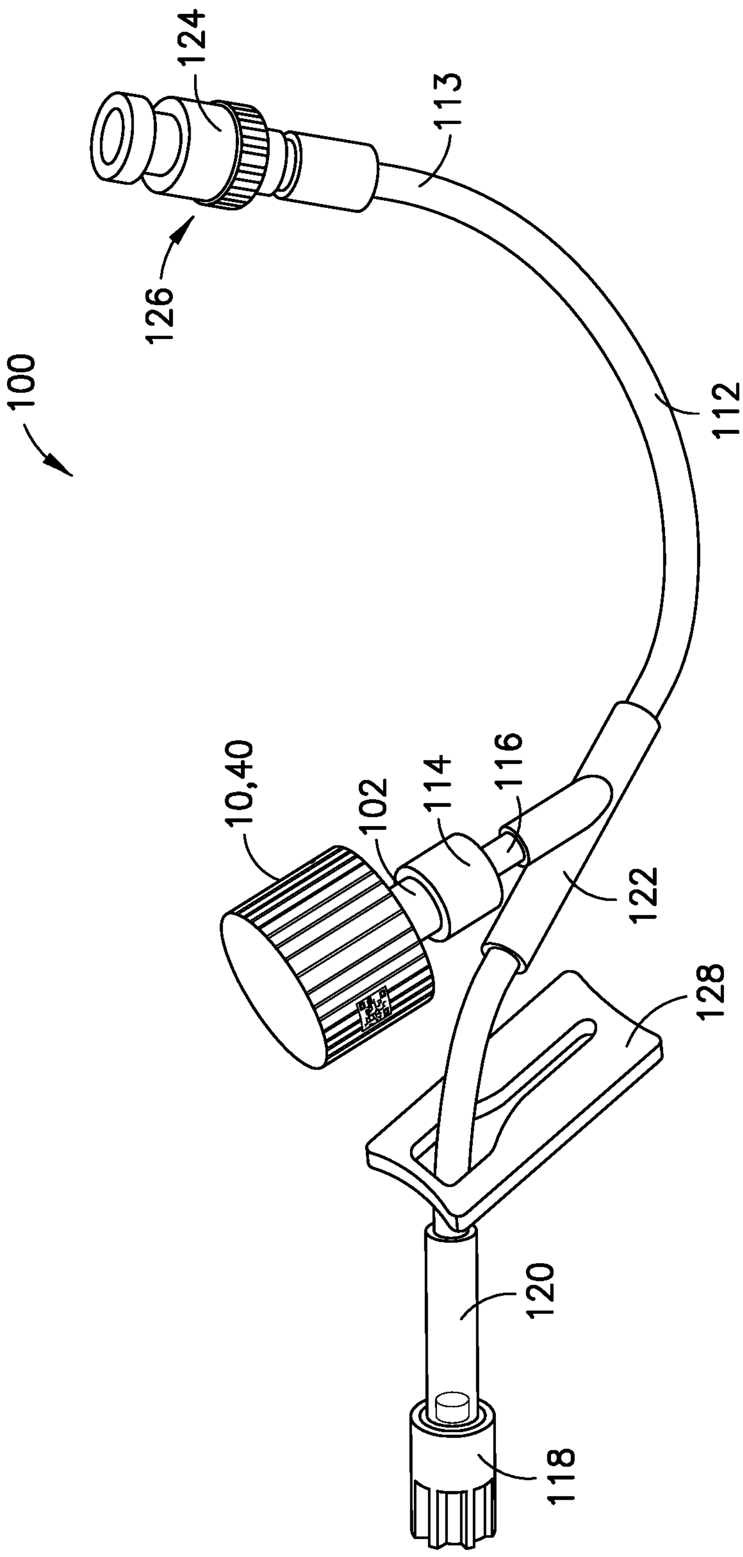
FIG. 6 is an assembled, perspective view of a drug transfer assembly in accordance with an embodiment of the present invention.
Figure 7:
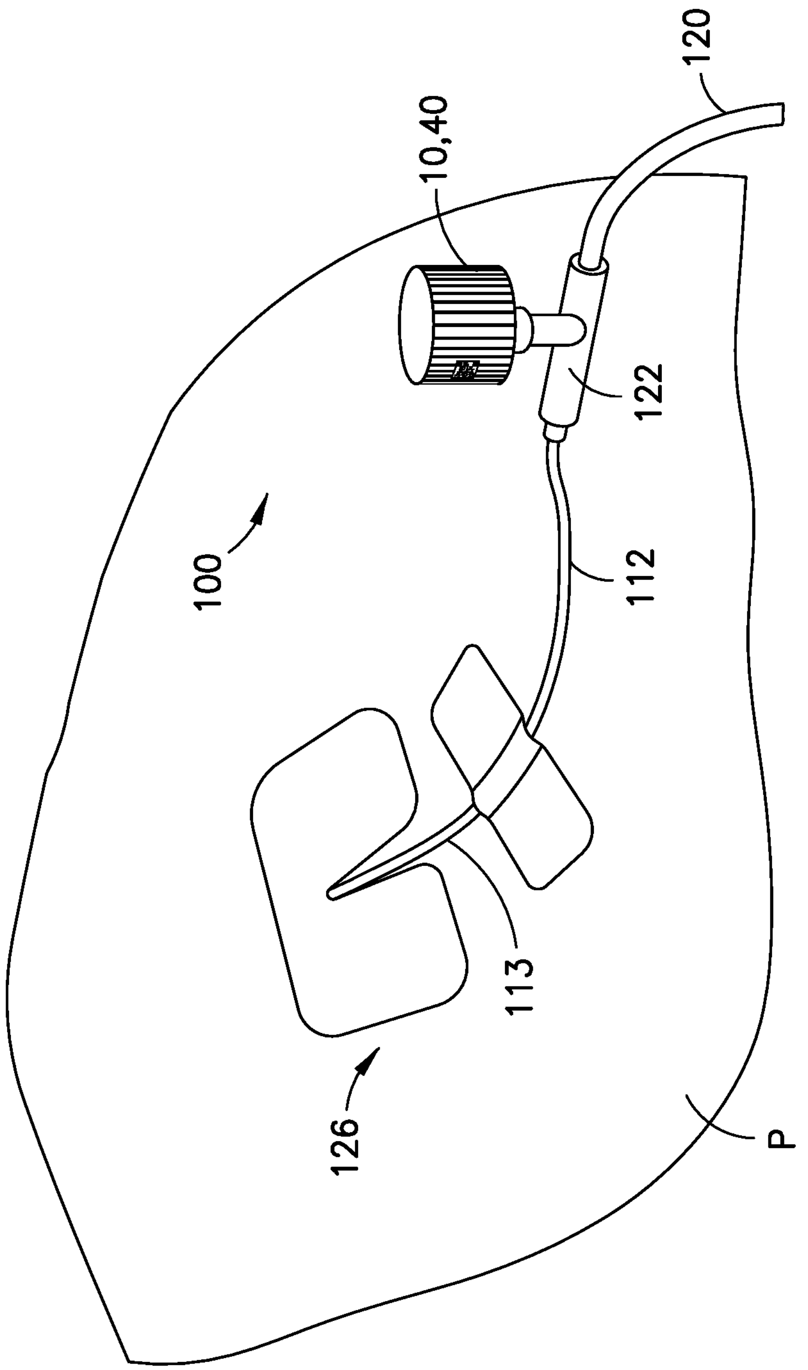
FIG. 7 is a perspective view of the drug transfer assembly of FIG. 6 with the drug transfer assembly provided to a patient in accordance with an embodiment of the present invention.
Figure 8:
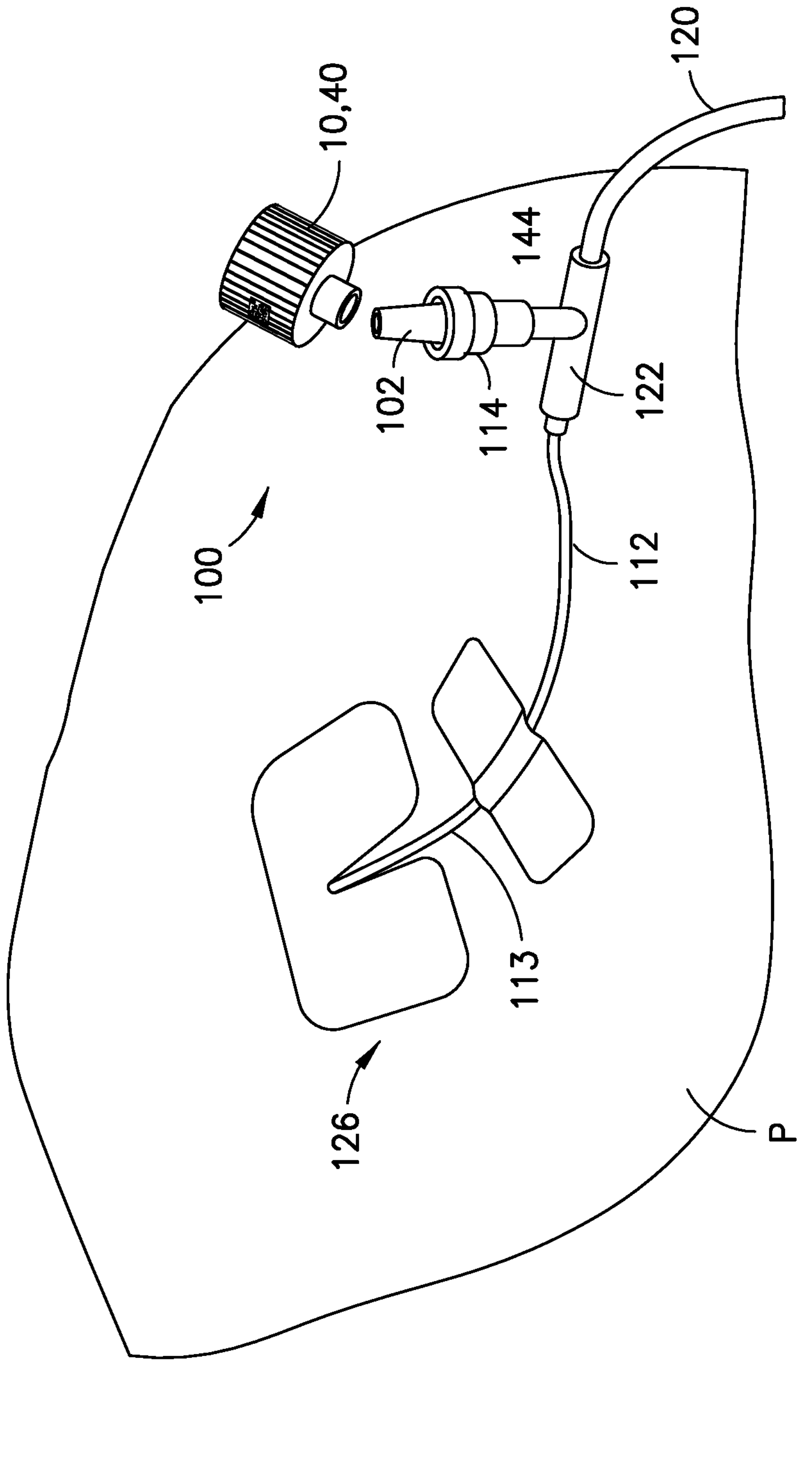
FIG. 8 is an exploded, perspective view of the drug transfer assembly of FIG. 7 with a medical device cap for connection with an IV access port of the drug transfer assembly removed in accordance with an embodiment of the present invention.

Referring to FIGS. 6-9, in one embodiment, a medical device cap 10, 40 of the present disclosure is removably connectable with a medical device component of a drug transfer assembly 100. The drug transfer assembly 100 includes an IV access port 102 and an intravenous line 112 adapted for connection to a bloodstream of a patient P. Drug transfer assembly 100 further includes a patient portion 113 of intravenous line 112, a first connector 114 connected to a first portion 116 of intravenous line 112, a second connector 118 connected to a second portion 120 of intravenous line 112, an intravenous line connector 122 for connecting in fluid communication patient portion 113 of intravenous line 112 with first portion 116 and second portion 120 of intravenous line 112, a patient connector 124 disposed at a patient end 126 of intravenous line 112, and a medical device cap 10, 40 of the present disclosure is removably connectable with a medical device component of the drug transfer assembly 100. For example, the medical device cap 10, 40 is removably connectable with IV access port 102 as shown in FIGS. 6-8.

Figure 9:
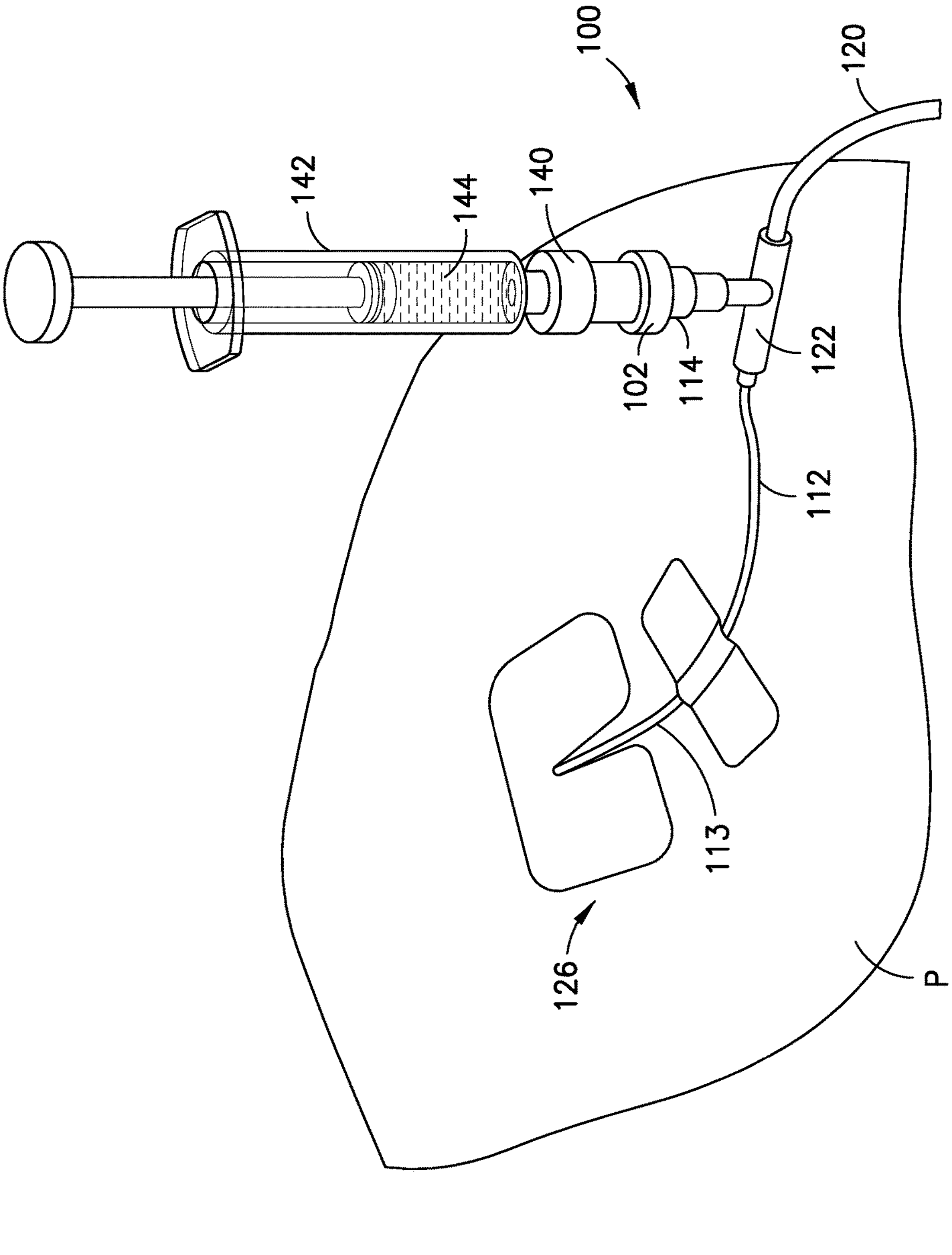
FIG. 9 is a perspective view of the drug transfer assembly of FIG. 7 with an injector connected to the IV access port of the drug transfer assembly in accordance with an embodiment of the present invention.

Referring to FIGS. 6-9, in one embodiment, intravenous line 112 may comprise sections of flexible plastic tubing. The sections of plastic tubing may be connected in fluid communication by intravenous line connector 122. In one embodiment, intravenous line connector 122 may comprise a Y-shape as shown in FIG. 6. In another embodiment, intravenous line connector 122 may comprise a T-shape as shown in FIGS. 7-9. Further, it is contemplated that intravenous line connector 122 may be made available in a variety of shapes and sizes to accommodate sections of plastic tubing so that first connector 114 and second connector 118 are spaced a distance from one another.

In one embodiment, first connector 114 comprises a connector which is compatible with components of closed system drug transfer devices. In one embodiment, second connector 118 comprises an intravenous bag connector which is adapted to receive an intravenous bag containing a medication. In other embodiments, second connector 118 comprises a connector which is compatible with components of closed system drug transfer devices.

Referring to FIG. 6, in one embodiment, drug transfer assembly 100 further includes a clamp 128 which can be used to temporarily restrict the flow of fluid within second portion 120 of the intravenous line 112.

The drug transfer assembly 100 of the present disclosure may be used with personal intravenous therapy applications that allow patients to receive infusion and medication treatment at home, although the drug transfer assembly 100 may also be used in any medical care setting. Home therapies may include the administration of medications by IV using intravenous and subcutaneous or hypodermis routes, i.e., into the bloodstream and under the skin. Examples of medical treatments that personal intravenous therapy applications may provide to a patient include antibiotics, pain management medications, cancer treatments, and similar medications.

Medications may be packaged as pre-filled devices, wherein a syringe assembly is pre-filled with medication prior to being packaged and delivered to a patient. Such pre-filled devices eliminate the need for a user to fill the device prior to injection.

Certain drugs or medications are preferably provided in powder or dry form (such as a lyophilized form), and require reconstitution prior to administration. Lyophilized drugs, for example, typically are supplied in a freeze-dried form that require mixing with a diluent to reconstitute the substance into a form that is suitable for injection. In addition, drugs may be provided as multipart systems that require mixing prior to administration. For example, one or more liquid components, such as flowable slurries, and one or more dry components, such as powdered or granular components, may be provided in separate containers that require mixing prior to administration.

Referring to FIG. 9, drug transfer assembly 100 includes an injector 140 that is removably connectable with IV access port 102 via first connector 114 and a syringe assembly 142 containing a medication or fluid 144. Medication 144 can be packaged within syringe assembly 142 as a "pre-filled" device or medication 144 may be a reconstituted medication as discussed above. Once the medication 144 is contained within syringe assembly 142, the medication 144 is ready for administration to a bloodstream of a patient such as patient P (FIGS. 7-9). Once a patient or medical practitioner is ready to administer the medication 144, the patient or medical practitioner may remove a medical device cap 10, 40 (FIG. 8) from IV access port 102 as will be described in further detail below.

Referring to FIG. 9, the patient P may then connect injector 140 to the IV access port 102 via first connector 114 that is connected to first portion 116 of intravenous line 112 of drug transfer assembly 100. Syringe assembly 142 may then be connected with injector 140. In one embodiment, injector 140 and syringe assembly 142 form a single component that is connected to the IV access port 102 via first connector 114. With injector 140 connected to the IV access port 102 via first connector 114, first connector 114 provides a secure, closed connection with injector 140 and syringe assembly 142 at the IV access port 102 that provides a leak-proof seal throughout a drug transfer procedure. Further, first connector 114 connects, in fluid communication, injector 140 and syringe assembly 142 with intravenous line 112 as shown in FIG. 9. In this manner, the patient P may inject medication 144 to their bloodstream. In such an embodiment, medication 144 can be injected into patient P through syringe assembly 142 to injector 140 to the IV access port 102 via first connector 114 and through first portion 116 of intravenous line 112 to intravenous line connector 122 to patient portion 113 of intravenous line 112 and through patient connector 124 at patient end 126 of intravenous line 112 to the bloodstream of the patient P in a secured, leak-proof, closed connection, i.e., in a manner such that no outside contaminants can enter into the drug transfer assembly 100 and such that no medication may leak from drug transfer assembly 100 during its travel through the above-described flow path.

Once the dose of medication has been administered, injector 140 and syringe assembly 142 are removed from first connector 114. In this configuration, IV access port 102 is exposed to the environment and may become contaminated with undesirables. To eliminate the IV access port 102 being exposed to the environment and becoming contaminated with undesirables, a medical device cap 10, 40 of the present disclosure is connected to the IV access port 102 via first connector 114 when a patient is done administering a dose of medication as shown in FIG. 7. In this manner, a medical device cap 10, 40 of the present disclosure protectively surrounds and shields the IV access port 102 to prevent contamination of the IV access port 102.

A medical device cap 10, 40 of the present disclosure also is able to record and transmit information when the medical device cap 10, 40 is connected to the IV access port 102. For example, a medical device cap 10, 40 is able to record and transmit a first piece of information when the medical device cap 10, 40 is connected to the IV access port 102. The first piece of information may comprise any information related to the medical device cap, the medical device component that the medical device cap is being coupled to, or the coupling event between the medical device cap and the medical device component. For example, the first piece of information may comprise time information, frequency information, medical device cap information, medical device component information, or other pertinent information.

A medical device cap 10, 40 of the present disclosure is uniquely tagged with an identification element such that variables related to the application of the medical device cap to a medical device component can be documented by reading the unique identification to obtain information contained within. When the medical device cap 10, 40 mates with an IV access port, a medical device with a luer tip, or other medical device component, the coupling event can be recorded and electronically documented to enable compliance and reduce infections. The coupling event can be recorded through technologies including, but not limited to, barcoding and RFID as described above. Better compliance and monitoring of the use of such medical device caps leads to reduced incidence of CRBSI related to IV access port contamination.

A medical device cap 10, 40 of the present disclosure through the unique identification technology coupled with an ID-decoding technology, would enable automated real-time electronic documentation of when the medical device cap is applied, while also documenting duration of application and tracking of devices for inventory management.

A medical device cap 10, 40 of the present disclosure also is able to record and transmit information when the medical device cap 10, 40 is removed from the IV access port 102. For example, a medical device cap 10, 40 is able to record and transmit a second piece of information when the medical device cap 10, 40 is removed from the IV access port 102. The second piece of information may comprise any information related to the medical device cap, the medical device component that the medical device cap is being coupled to, or the coupling event between the medical device cap and the medical device component. For example, the second piece of information may comprise time information, frequency information, medical device cap information, medical device component information, or other pertinent information.

As discussed above, a medical device cap 10, 40 of the present disclosure is removably connectable with a medical device component. Referring to FIG. 4, in one embodiment, the medical device cap 10, 40 is removably connectable with a luer tip 150. In one embodiment, the medical device cap is a luer tip cap or a medical device cap that is removably connectable with luer tip 150.

Referring to FIG. 5, in another embodiment, the medical device cap 10, 40 is removably connectable with an IV access port 160. In one embodiment, the medical device cap is an IV access port cap or a medical device cap that is removably connectable with IV access port 160.

Referring to FIGS. 4, 5, and 7, in an exemplary embodiment, a medical device cap 10, 40 and a medical device component are secured together by an interference fit connection to provide a secure fit therebetween, such that a medical device cap 10, 40 protectively surrounds and shields the medical device component to prevent contamination of the medical device component.

Referring to FIGS. 4 and 5, cap body 12 of medical device cap 10 and cap body 42 of medical device cap 40 are each sized and shaped to substantially correspond to an exterior profile 155 of luer tip 150 or an exterior profile 165 of IV access port 160. This interference fit between a medical device cap 10, 40 and a respective medical device component 150, 160 is achieved by sizing and shaping the two mating parts, i.e., the interior profile of a cap body 12, 42 of a medical device cap 10, 40 and the exterior profile 155, 165 of a medical device component 150, 160 so that the interior profile of cap body 12, 42 of medical device cap 10, 40 only slightly deviates dimensionally from the exterior profile 155, 165 of a medical device component 150, 160. This ensures an interference fit that secures a cap body 12, 42 of a medical device cap 10, 40 and a respective medical device component 150, 160 together by a friction force after insertion of a medical device component 150, 160 into a selected medical device cap 10, 40 as shown in FIGS. 4 and 5.

In other embodiments, a medical device cap 10, 40 and a medical device component are secured together by other connection means to provide a secure fit therebetween, such that a medical device cap 10, 40 protectively surrounds and shields the medical device component to prevent contamination of the medical device component. For example, in other embodiments, the connection means may include a threaded portion, a snap fit mechanism, a ball detent, locking tabs, a spring loaded locking mechanism, latch, adhesive, or other similar mechanism.

A medical device cap 10, 40 of the present disclosure includes a unique identification element that contains information unique to that specific device and is capable of recording and transmitting any information related to the medical device cap, the medical device component that the medical device cap is being coupled to, or the coupling event between the medical device cap and the medical device component. This information can be read by a machine with certain capabilities to read the unique identification element of the medical device cap and electronically disseminating information for documentation purposes. For example, referring to FIG. 3, scanner 180 may be utilized for laser scanning of the barcodes. Additionally, the information can be read from the unique identification element of the medical device cap when the coupling of the medical device cap takes place with a medical device component and when the medical device cap is removed from the medical device component.

In other embodiments, a similar use of a unique identification element that contains information unique to that specific device and is capable of recording and transmitting information can also be used with IV access ports (Q-style) to enable documentation or coupling between uniquely tagged devices for compliance and/or inventory tracking/utilization purposes. In one embodiment, together with a Flush syringe, also having a similar unique identification element, a user could document any interaction between a device and an IV access port through the same principles as described above.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method, comprising:

connecting an IV access port cap for a drug transfer assembly to an IV access port of the drug transfer assembly, wherein the IV access port cap includes a cap body removably connectable with the IV access port via an interference fit connection that secures the cap body and the IV access port directly together by a friction force therebetween after insertion of the IV access port into the cap body, an identification element disposed on the cap body, and a disinfecting sponge disposed inside the cap body and including at least one cleaning or disinfecting agent that is released to contact the IV access port when the IV access port is inserted into the cap body to form the interference fit connection that secures the cap body and the IV access port directly together, and wherein the identification element contains a unique identifier associated with the IV access port cap;

reading, with a scanner that resides separately from the drug transfer assembly including the IV access port, when the IV access port cap is connected to the IV access port, the unique identifier associated with the IV access port cap from the identification element to record when the IV access port cap is connected to the IV access port;

removing the IV access port cap from the IV access port; and reading, with the scanner that resides separately from the drug transfer assembly including the IV access port, when the IV access port cap is removed from the IV access port, the unique identifier associated with the IV access port cap from the identification element to record a duration of time that the cap body is connected to the IV access port for a disinfectant application and a frequency that the cap body is disconnected from the IV access port for the disinfection application.

2. The method of claim 1, wherein with the cap body connected to the IV access port, the cap body protectively surrounds at least a portion of the IV access port.

3. The method of claim 1, wherein the identification element comprises a barcode.

4. The method of claim 3, wherein the barcode is disposed on a cap exterior wall of the cap body.

5. The method of claim 1, wherein the identification element comprises an RFID.

6. A method, comprising:

connecting a medical device cap for a drug transfer assembly to a luer tip of the drug transfer assembly, wherein the medical device cap includes a cap body removably connectable with the luer tip via an interference fit connection that secures the cap body and the luer tip directly together by a friction force therebetween after insertion of the luer tip into the cap body, an identification element disposed on the cap body, and a disinfecting sponge disposed inside the cap body and including at least one cleaning or disinfecting agent that is released to contact the luer tip when the luer tip is inserted into the cap body to form the interference fit connection that secures the cap body and the luer tip directly together, and wherein the identification element contains a unique identifier associated with the medical device cap;

reading, with a scanner that resides separately from the drug transfer assembly including the luer tip, when the medical device cap is connected to the luer tip, the unique identifier associated with the medical device cap from the identification element to record when the medical device cap is connected to the luer tip;

removing the medical device cap from the luer tip; and reading, with the scanner that resides separately from the drug transfer assembly including the luer tip, when the medical device cap is removed from the luer tip, the unique identifier associated with the medical device cap from the identification element to record a duration of time that the cap body is connected to the luer tip for a disinfection application and a frequency that the cap body is disconnected from the luer tip for the disinfection application.

7. The method of claim 6, wherein with the cap body connected to the luer tip, the cap body protectively surrounds at least a portion of the luer tip.

8. The method of claim 6, wherein the identification element comprises a barcode.

9. The method of claim 8, wherein the barcode is disposed on a cap exterior wall of the cap body.

10. The method of claim 6, wherein the identification element comprises an RFID.

11. A system, comprising:

an IV access port cap for a drug transfer assembly configured to be connected to an IV access port of the drug transfer assembly, wherein the IV access port cap includes a cap body removably connectable with the IV access port via an interference fit connection that secures the cap body and the IV access port directly together by a friction force therebetween after insertion of the IV access port into the cap body, an identification element disposed on the cap body, and a disinfecting sponge disposed inside the cap body and including at least one cleaning or disinfecting agent that is released to contact the IV access port when the IV access port is inserted into the cap body to form the interference fit connection that secures the cap body and the IV access port directly together, and wherein the identification element contains a unique identifier associated with the IV access port cap; and a scanner that resides separately from the drug transfer assembly including the IV access port, wherein the scanner is configured to: (i) read, when the IV access port cap is connected to the IV access port, the unique identifier associated with the IV access port cap from the identification element to record when the IV access port cap is connected to the IV access port and (ii) read, when the IV access port cap is removed from the IV access port, the unique identifier associated with the IV access port cap from the identification element to record a duration of time that the cap body is connected to the IV access port for a disinfection application and a frequency that the cap body is disconnected from the IV access port for the disinfection application.

12. The system of claim 11, wherein the IV access port cap is configured to be connected to a luer tip of the drug transfer assembly.

13. The system of claim 11, wherein the identification element comprises a barcode.

14. The system of claim 11, wherein the barcode is disposed on a cap exterior wall of the cap body.

15. The system of claim 11, wherein the identification element comprises an RFID.

* * * * *